United States Patent [19]

Nishizawa et al.

[11] Patent Number: 5,010,299

[45] Date of Patent: Apr. 23, 1991

[54] METHOD FOR MEASURING STRESS ON STEEL BY DETERMINING THE REVERSE MAGNETIC PERMEABILITY UNDER A MAGNETIC BIAS FIELD

[75] Inventors: Hidekazu Nishizawa, Osaka; Tomoaki Utsunomiya, Ehime, both of Japan

[73] Assignee: Nikkoshi Co., Ltd., Tokyo, Japan

[21] Appl. No.: 491,423

[22] Filed: Mar. 9, 1990

[30] Foreign Application Priority Data

Mar. 17, 1989 [JP] Japan .................................. 1-65364

[51] Int. Cl.$^5$ ........................ G01B 7/24; G01R 33/18
[52] U.S. Cl. .................................................. 324/209
[58] Field of Search ...................................... 324/209

[56] References Cited

FOREIGN PATENT DOCUMENTS 63-26112 10/1988 Japan .

Primary Examiner—Walter E. Snow
Attorney, Agent, or Firm—Wenderoth, Lind & Ponack

[57] ABSTRACT

A rapid and reliable non-destructive method is proposed for the determination of stress in a steel material by determining the reversible magnetic permeability $\mu$ under a magnetic bias field $H_0$ in the range of approach to the saturation magnetization, calculating the factor M in the equation $\mu = 1 + M/H_0^3$ by using the value of $\mu$, and calculating $\sigma_1$, $\sigma_2$ and $\theta$ by solving the equation $$\sqrt{M} = a + b[(\sigma_1 + \sigma_2) + 3(\sigma_1 - \sigma_2)\cos 2\theta],$$

in which $\sigma_1$ is a principal stress, $\sigma_2$ is the principal stress perpendicular to $\sigma_1$, $\theta$ is the angle between $\sigma_1$ and the direction of measurement of $\mu$, a is the value of $\sqrt{M}$ in a stress-free state and b is the stress sensitivity, a and b being determined separately.

2 Claims, 2 Drawing Sheets

FIG. 1a
FIG. 1b
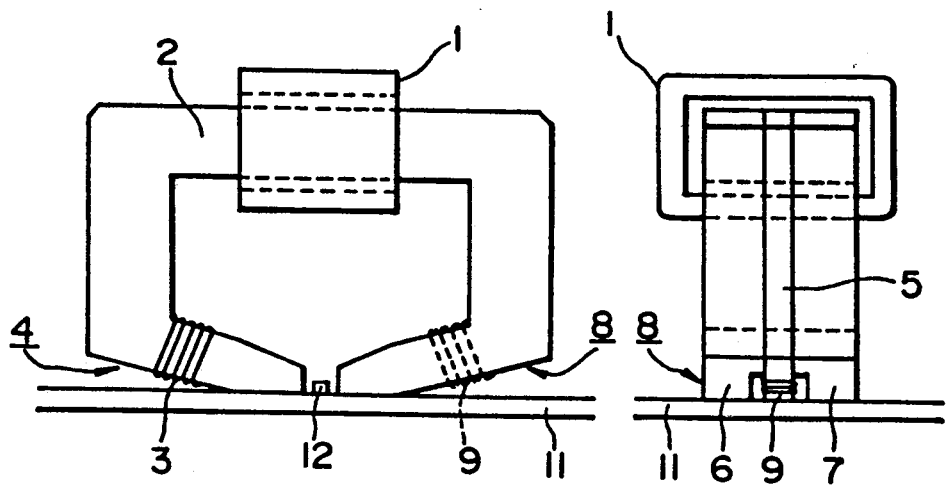
FIG. 1c
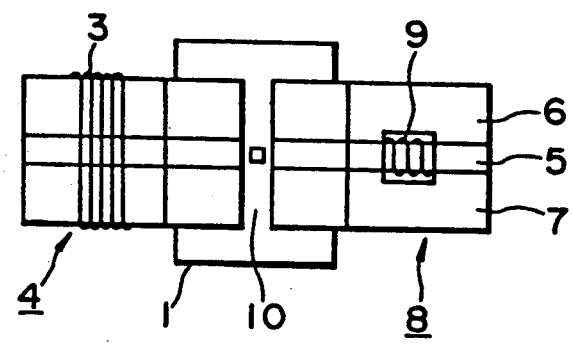
FIG. 2
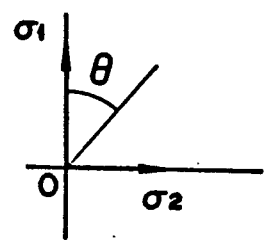

METHOD FOR MEASURING STRESS ON STEEL BY DETERMINING THE REVERSE MAGNETIC PERMEABILITY UNDER A MAGNETIC BIAS FIELD

BACKGROUND OF THE INVENTION

The present invention relates to a method for the determination of stress applied to a steel material constituting a structural body in the fields of architecture, civil engineering, machinery and the like. More particularly, the invention relates to a reliable and rapid non-destructive method for the determination of the principal stress and the direction thereof in a steel material.

Several methods utilizing magnetism are known in the prior art for the determination of a stress applied to a steel material including a method by utilizing the changes in the magnetic permeability caused by the stress and a method utilizing the changes in the Barkhausen noise caused by the stress. The former method utilizes the principle that the magnetic permeability varies in proportion to the difference in the principal stresses for the determination of the principal stresses and the directions thereof. The latter method utilizes the principle that the Barkhausen noise is varied correspondingly to the principal stress for the determination thereof.

The above mentioned conventional magnetic methods for the stress determination each have a problem in the reliability. For example, no reproducible results can be obtained due to the phenomenon of hysteresis inherent in the magnetic measurements. Since the measurement is performed in the range of the magnetic field which is approximately of the same order as the coercive force of the steel materials, in addition, a large error is unavoidable in the result of the determination when the steel material has residual magnetizatism. Moreover, each of these prior art methods is an empirical method merely based on the observed facts with no established theoretical ground so that the methods are subject to a limitation relative to the versatility in the application to a variety of materials.

SUMMARY OF THE INVENTION

The present invention accordingly has an object to provide a novel and improved magnetic method for the determination of stress in a steel material free from the above described problems in the prior art methods.

Thus, the method of the invention for the determination of a stress in a steel material comprises the steps of:

(a) determining the reversible magnetic permeability $\mu$ by using a stress detector of steel materials utilizing the phenomenon of magnetostriction under a magnetic bias field $H_0$ within the range of approach to the saturation magnetization;

(b) calculating the value of M, which is the first-order factor on $1/H_0^3$ for the reversible magnetic permeability $\mu$ of the steel material, utilizing the values of $\mu$; and (c) calculating the values of a principal stress $\sigma_1$ in the steel material which is in the direction perpendicular to the direction of $\sigma_1$ and the angle $\theta$ between the direction of $\sigma_1$ and the direction at which the reversible magnetic permeability $\mu$ is determined, from the equation $$\sqrt{M} = a + b[(\sigma_1 + \sigma_2) + 3(\sigma_1 - \sigma_2)\cos 2\theta], \quad (I)$$

in which a is the value of the square root of M in a stress-free state and b is the stress sensitivity.

BRIEF DESCRIPTION OF THE DRAWING

FIGS. 1a, 1b and 1c are each a schematic illustration of a front view, side view and bottom view, respectively, of the stress detector utilizing the phenomenon of magnetostriction and used in practicing the method of the invention.

FIG. 2 is a vector diagram showing the relationship between the directions of the principal stresses and the detector head.

DETAILED DESCRIPTION OF THE PREFERRED EMBODIMENTS

Figure 3:
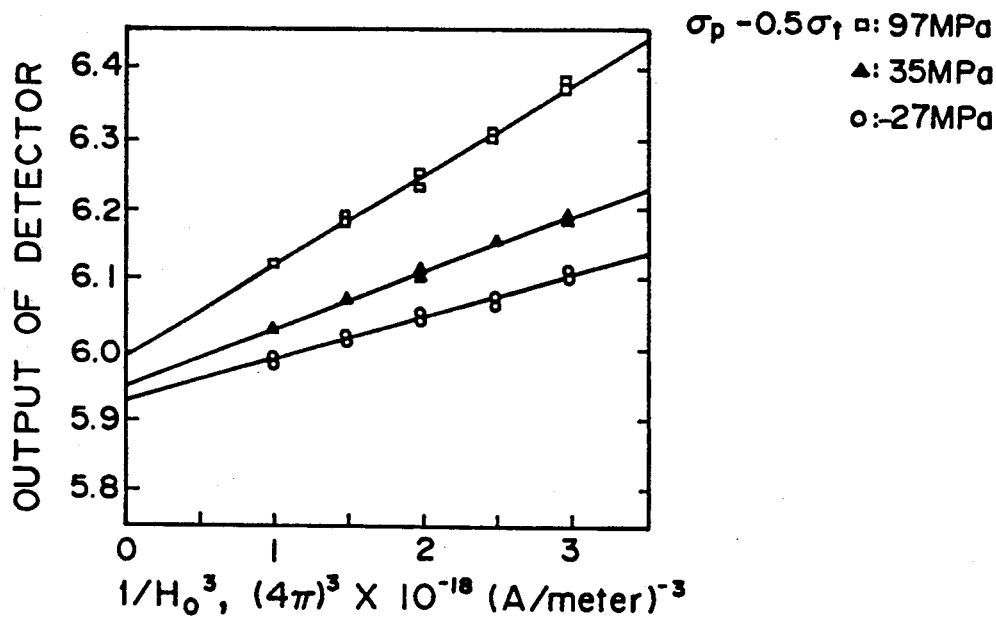
FIG. 3 is a graph showing the output of the detector as a function of the magnetic bias field.

In the following, the method of the invention is described in detail with reference to the accompanying drawing.

FIGS. 1a, 1b and 1c are each a front view, side view and bottom view, respectively, of the stress detector utilizing the phenomenon of magnetostriction and used in practicing the method of the invention. This stress detector is disclosed in detail in Japanese Patent Kokai 63-261124. In this apparatus, a bias coil 1 producing a magnetic bias field surrounds the body 2 of the yoke and one of the legs 4 of the yoke is surrounded by a coil 3. The yoke has a sandwich structure consisting of a center yoke 5 sandwiched by two guard yokes 6,7 and the leg 8 of the center yoke 5 opposite to the leg 4 is surrounded by a search coil 9 which serves to detect the alternating-current magnetic flux produced in the center yoke 6 when the coil 3 is energized with an alternating current. The legs 4 and 8 of the yoke are directly contacted with the steel material 11 under measurement while a Hall element 12 is placed within the gap 10 between the legs 4,8 to serve for the determination of the magnetic bias field and the alternating-current magnetic field.

To describe the principle of the present invention in more detail, a direct-current bias magnetic field $H_0$ is applied within the yoke as being overlapped by the alternating-current magnetic field of a very small amplitude $\Delta H$ and the amplitude $\Delta B$ of the alternating-current magnetic flux density through the center core is measured to determine the reversible magnetic permeability $\mu = \Delta B/\Delta H$ in the range of the rotational magnetic field of the steel member from which the stress is detected.

As illustrated in FIGS. 1a-c, the detector of the present invention is constituted such that the bias coil 1, in order to generate a high direct-current bias magnetic field, surrounds the body 2 of the U-shaped yolk and an alternating-current exciting coil 3, in order to generate an alternating current magnetic field of a small amplitude, surrounds the leg 4 of the U-shaped yolk. On the other hand, the search coil 9, in order to detect the changes in the magnetic flux density within the center core or, namely the member under measurement, is arranged such as to surround the center core of the yolk leg 8 and, further, a sensor 12 is provided to monitor the magnetic field applied to the member under measurement at the center between the legs of the yolk.

What is important here is that the m portions of the yolk legs 4 and 8 are divided such that the outer two guard yolk 6, 7 prevent the fusion of the magnetic field generated in the center core 5 so as to generate a magnetic field of uniform distribution in a definite direction within the member or steel material under measurement. See FIG. 1b.

According to the present invention, it is possible to measure the reverse magnetic permeability of the portion of the steel member under measurement where the magnetic flux passes through as coming out of the center core of one leg and entering the center core of the other leg so as accurately detect the stress acting thereon.

Assuming that the crystalline magnetic anisotropy constant of a ferromagnetic material of the cubic crystalline system is K and the saturation magnetization of the material is Is, then the unitarity of the magnetized state is held only when the magnetic field is equal to or larger than the critical magnetic field $H_{crit}$ given by the equation $$H_{crit} = 2K/Is.$$

The range of magnetic field satisfying the above mentioned requirement is usually called the range of approach to thec magnetic saturation. The value for iron is around 50 kA/meter. The largest feature in the inventive method consists in conducting the magnetic measurement in such a range of the much higher magnetization than in the conventional magnetic methods so as to ensure complete disappearance of the disturbing influences by the phenomenon of magnetic hysteresis or the residual magnetization of the material under measurement, which is supported not only by the theory but also by the experimental results.

When a magnetic bias field $H_0$ is added to the magnetic field in this range of magnetization by means of the bias coil 1, it is known that a relationship called the law of approach to magnetic saturation is held as expressed by the equation $$\mu \approx 1 + M/H_0^3, \quad (II)$$

in which M is the first-order factor on $1/H_0^3$ for $\mu$.

When the above described stress detector is put to work in the direction making an angle $\theta$ with the direction of the principal stress $\sigma_1$ and the reversible permeability $\mu$ is determined for a specified value of $H_0$ from which the first-order factor M is calculated, it has been found that the square root of M is given as a function of the stress according to the equation $$\sqrt{M} = a + b[(\sigma_1 + \sigma_2) + 3(\sigma_1 - \sigma_2)\cos 2\theta], \quad (I)$$

in which $\sigma_1$ and $\sigma_2$ are the principal stresses in the directions perpendicular to each other, a is the value of the square root of M in a stress-free state and b is the stress sensitivity. The values of a and b can be determined separately by using a test piece of the same steel material as the steel material under measurement. This equation is derived for abiaxially stressed state but it is applicable also to the state of uniaxial stress by putting $\sigma_2$ equal to zero.

In the following, standard procedures are described for practicing the method of the invention by using the above described stress detector.

(1) When the principal stresses and the direction thereof are unknown

The values of the reversible permeability $\mu$ are determined in three or more directions not in parallel with each other and the values are substituted for $\mu$ in the equation (II) from which three or more values of M are calculated for the respective directions. These values of M are then substituted for M in the equation (I) to give a set of three simultaneous equations from which the values of $\sigma_1$, $\sigma_2$ and $\theta$ can be determined.

(2) When the principal stresses are unknown but the directions thereof are known Values of the reversible permeability $\mu$ are determined in two directions of the principal stresses $\sigma_1$ and $\sigma_2$, i.e. in the directions of $\theta = 0°$ and $\theta = 90°$, and the values of M, i.e. $M_1$ and $M_2$, are calculated therefrom by using the equation (II). The thus obtained values of $M_1$ and $M_2$ are substituted in the following equation to give a set of two simultaneous equations from which the values of $\sigma_1$ and $\sigma_2$ are calculated:

$$\begin{pmatrix} \sigma_1 \\ \sigma_2 \end{pmatrix} = (\tfrac{1}{4}b) \begin{pmatrix} 1 & 0.5 \\ 0.5 & 1 \end{pmatrix} \begin{pmatrix} \sqrt{M_1} - a \\ \sqrt{M_2} - a \end{pmatrix}.$$

(3) When the stress is uniaxial

The reversible magnetic permeability $\mu$ is determined in the direction of the stress and the value is substituted in the equation (II) to give the value of M, from which the stress $\sigma$ is obtained by using the equation $$\sigma = (\sqrt{M} - a)/4b.$$

Alternatively, the value of $\sigma$ can be calculated from the equation $$\sigma = (\sqrt{M_p} - \sqrt{M_t})/6b,$$

in which $M_p$ and $M_t$ are the values of M in the direction of the stress and in the direction perpendicular to the direction of the stress, respectively. Note that this equation does not involve a.

Following is a description of an example of the inventive method.

Figure 4:
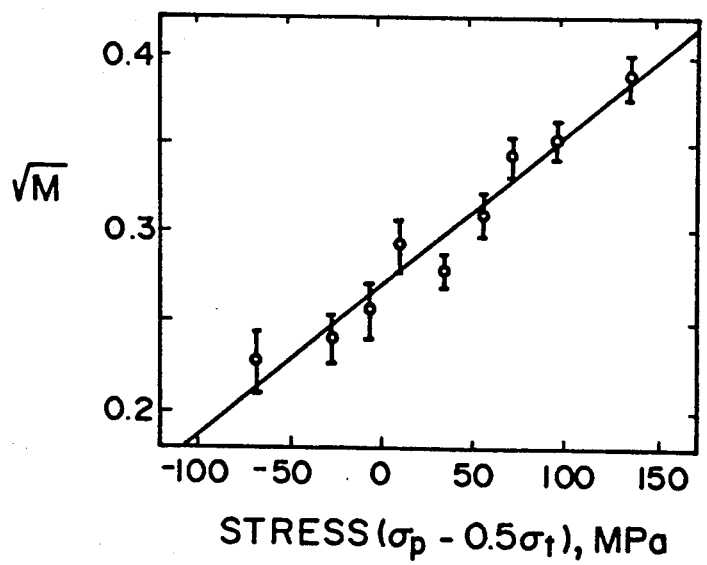
FIG. 4 is a graph showing the value of $\sqrt{M}$ as a function of the principal stress.

The detector illustrated in FIGS. 1a, 1b and 1c was applied to a test piece of a steel of the SS41 grade having a thickness of 3.2 mm in the form of a cross of 90° revolutionary symmetry under a constant stress and the output of the detector, which is proportional to the reversible permeability $\mu$, was recorded with the magnetic bias field $H_0$ varied to have values of 1.000, 0.874, 0.794, 0.737 and $0.693 \times 10^6/4\pi$ A/meter. The measurement was performed for various values of $(\sigma_p - 0.5\sigma_t)$, in which $\sigma_p$ is the principal stress in the direction of measurement and $\sigma_t$ is the principal stress in the direction perpendicular to $\sigma_p$. The results of the detector output are shown in FIG. 3 as a function of $1/H_0^3$. A straight line was obtained for each stress. The gradient of the straight line gives the value of M. FIG. 4 is a graph obtained by plotting the value of $\sqrt{M}$ against the stress $(\sigma_p - 0.5\sigma_t)$. Good linearity was obtained also.

As is understood from the above given description, the inventive method of stress determination is highly reliable not only theoretically but also experimentally and the procedure is very simple and non-destructive so that the method is very useful as a method for the stress determination in steel materials undertaken on the working site in the fields of architecture, civil engineering and the like where destructive methods can hardly be applicable.

What is claimed is:

1. A method for the determination of a stress in a steel material which comprises the steps of:
   (a) determining the reversible magnetic permeability $\mu$ by using a stress detector of steel materials utilizing the phenomenon of magnetostriction under a magnetic bias field $H_0$ within the range of approach to the saturation magnetization;
   (b) calculating the value of M, which is the first-order factor on $1/H_0^3$ for the reversible magnetic permeability $\mu$ of the steel material in the equation $\mu = 1 + M/H_0^3$, utilizing the values of $\mu$; and
   (c) calculating the values of a principal stress $\sigma_1$ in the steel material, the other principal stress $\sigma_2$ in the steel material which is in the direction perpendicular to the direction of $\sigma_1$ and the angle $\theta$ between the direction of $\sigma_1$ and the direction at which the reversible magnetic permeability $\mu$ is determined, from the equation $$\sqrt{M} = a + b[(\sigma_1 + \sigma_2) + 3(\sigma_1 - \sigma_2)\cos 2\theta],$$

in which a is the value of the square root of M in a stress-free state and b is the stress sensitivity.

2. A method for the determination of a stress in a steel material which comprises the steps of:
   (a) determining the reversible magnetic permeability $\mu$ by using a stress detector of steel materials utilizing the phenomenon of magnetostriction under a magnetic bias field $H_0$ within the range of approach to the saturation magnetization in at least three directions not parallel to each other;
   (b) calculating the values of M, which is the first-order factor on $1/H_0^3$ for the reversible magnetic permeability $\mu$ of the steel material in the equation $\mu = 1 + M/H_0^3$, utilizing the three values of $\mu$ obtained in step (a); and
   (c) calculating the values of a principal stress $\sigma_1$ in the steel material, the other principal stress $\sigma_2$ in the steel material which is in the direction perpendicular to the direction of $\sigma_1$ and the angle $\theta$ between the direction of $\sigma_1$ and the direction at which the reversible magnetic permeability $\mu$ is determined, by solving a set of at least three simultaneous equations obtained by substituting the three values of M obtained in step (b) in the equation $$\sqrt{M} = a + b[(\sigma_1 + \sigma_2) + 3(\sigma_1 - \sigma_2)\cos 2\theta],$$

in which a is the value of the square root of M in a stress-free state and b is the stress sensitivity.

* * * * *